United States Patent [19]

Crosby

[11] 4,259,263
[45] Mar. 31, 1981

[54] HALOGENATED HYDROCARBONS AND A METHOD FOR THEIR PREPARATION

[75] Inventor: John Crosby, Manchester, England

[73] Assignee: Imperial Chemical Industries Limited, London, England

[21] Appl. No.: 80,326

[22] Filed: Oct. 1, 1979

[30] Foreign Application Priority Data

Oct. 26, 1978 [GB] United Kingdom ............... 41988/78

[51] Int. Cl.³ .............................................. C07C 21/18
[52] U.S. Cl. .................................................... 570/135
[58] Field of Search ............................ 260/653.5, 653.3

[56] References Cited

U.S. PATENT DOCUMENTS 2,700,688   1/1955   Crane et al. .................... 260/653.5

*Primary Examiner*—Delbert E. Gantz
*Assistant Examiner*—Joseph A. Boska
*Attorney, Agent, or Firm*—Cushman, Darby & Cushman

[57] ABSTRACT

A halogenated hydrocarbon having the general formula:

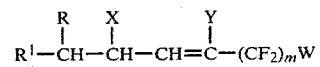

wherein Y represents fluorine, chlorine, bromine or $-(CF_2)_mW$, R represents hydrogen or lower alkyl, $R^1$ represents lower alkyl, X represents chlorine, bromine or iodine, W represents hydrogen, fluorine or chlorine and m is 1 or 2, is prepared by heating a compound having the general formula:

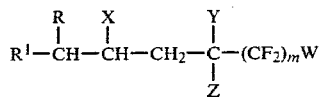

wherein R, $R^1$, X, Y, W and m have the meanings given above and Z represents chlorine, bromine or iodine, in a polar aprotic solvent together with an alkanolamine, optionally in the presence of a copper salt.

4 Claims, No Drawings

HALOGENATED HYDROCARBONS AND A METHOD FOR THEIR PREPARATION

This invention relates to halogenated hydrocarbons, useful as insecticide intermediates, and to a method for their preparation.

According to the present invention there is provided a halogenated hydrocarbon having the general formula:

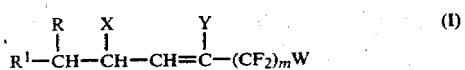

wherein Y represents a fluorine, chlorine or bromine atom, or $(CF_2)_mW$, R represents a hydrogen atom or a lower alkyl group, $R^1$ represents a lower alkyl group, X represents a chlorine, bromine or iodine atom, W represents hydrogen, fluorine or chlorine and m is 1 or 2.

Preferably X and Y represent chlorine or bromine atoms, especially chlorine atoms.

By "lower alkyl group" we mean an alkyl group containing from 1 to 6 carbon atoms, preferably a methyl group.

A specific example of a halogenated hydrocarbon of formula (I) is 2,4-dichloro-5-methyl-1,1,1-trifluorohex-2-ene.

According to a further feature of the invention there is provided a process for the manufacture of a halogenated hydrocarbon of formula (I) which comprises heating in a polar aprotic solvent, together with an alkanolamine, optionally in the presence of a copper salt, a halogenated hydrocarbon having the general formula:

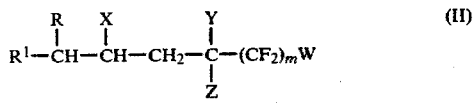

wherein R, $R^1$, X, Y, W and m have the meanings defined above and Z represents a chlorine, bromine or iodine atom.

Examples of polar aprotic solvents which may be used in the above process are diethylformamide, hexamethylphosphoramide and especially dimethylformamide and dimethylacetamide.

The amount of polar aprotic solvent which is used may be from 1 to 100 moles, preferably 3 to 15 moles per mole of the starting material of formula (II).

Examples of the alkanolamines which may be used are monoethanolamine, monoisopropanolamine and diethanolamine.

The amount of alkanolamine which is used may be from 1 to 100 moles, preferably 1 to 10 moles per mole of the compound of formula (II).

An example of a copper salt which may be included is cuprous chloride.

The copper salt may be used in a amount from $10^{-4}$ to $10^{-1}$ moles, conveniently $10^{-3}$ to $10^{-2}$ moles per mole of the compound of formula (II).

The reaction may be carried out at a temperature from 20° to 200° C., conveniently from 50° to 150° C., and may require a reaction time of several minutes to several days.

The progress of the reaction can be followed by analytical sampling of the reaction mixture, for example, by gas-liquid chromatographic (GLC) analysis.

Reaction is preferably carried out under an inert atmosphere, for example, nitrogen.

Isolation of the reaction product is carried out by conventional means. For example, the product may be precipitated from solution in the polar aprotic solvent by addition of a solvent which is miscible with the polar aprotic solvent but in which the reaction product of formula (I) is insoluble. A suitable solvent for this purpose is water. The precipitated product may then be extracted from the aqueous mixture with an organic solvent, for example, dichloromethane, followed by removal of the organic solvent, if desired under reduced pressure, to give the product of formula (I).

The starting materials of formula (II), may be prepared by suitable classical processes of organic chemistry. However, especially useful processes comprise reacting an alkyl substituted butene with a polyhalogenated alkane having 2 to 4 carbon atoms, in the presence of a suitable catalyst, as more fully described in our copending United Kingdom patent Application of earlier date.

The halogenated hydrocarbons of formula (I) are useful as intermediates in the preparation of insecticides based on certain cyclopropanecarboxylic acids. Thus, the compounds of formula (I) may be dehydrohalogenated by heating in a polar aprotic solvent, for example, dimethylformamide preferably in the presence of an alkali metal halide, for example, lithium chloride, to give dienes of the general formula:

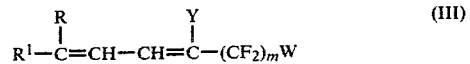

wherein R, $R^1$, Y, W and m have the meanings defined above. This process is more fully described in a copending United Kingdom patent application of earlier date.

A specific example of a compound of formula (III) which may be prepared as described above is 2-chloro-5-methyl-1,1,1-trifluorohexa-2,4-diene. The latter compound (1 mol proportion) may be reacted, for example, with ethyl bromocyanoacetate (1.5 mol proportions) in the presence of cuprous chloride (0.1 mol proportion) as catalyst and calcium carbonate (1.5 mol proportions) as base, in ethanol at reflux for ca. 12 hours, to give ethyl 3-(2-chloro-3,3,3-trifluoropropenyl)-1-cyano-2,2-dimethylcyclopropane-1-carboxylate, which may itself be converted by known methods into 3-(2-chloro-3,3,3-trifluoropropenyl)-2,2-dimethylcyclopropane-1-carboxylic acid or a lower alkyl ester thereof. This cyclopropane carboxylic acid or ester may be further esterified or transesterified respectively with, for example, m-phenoxybenzyl alcohol, to give a compound which is a potent insecticide.

The invention is illustrated but not limited by the following Examples.

EXAMPLE 1

A mixture comprising 5-methyl-2,2,4-trichoro-1,1,1-trifluorohexane (51.5 g), monoethanolamine (6.1 g), cuprous chloride (0.1 g) and dimethylformamide (100 ml) is stirred and heated at 96° C. (internal temperature) under a nitrogen atmosphere. When the initial green colour of the mixture is discharged further aliquots of monoethanolamine are added until a geen colour persists and GLC analysis shows that the starting material has been consumed. The reaction is complete after 5 hours. The crude product is isolated by precipitation with water, extraction with dichloromethane and removal of the solvent under reduced pressure. Distillation affords 2,4-dichloro-5-methyl-1,1,1,trifluorohex-2-ene (71%), b.p. 79°–82° C./100 mm Hg; 'Hnmr (CDCl$_3$)$\tau$9.2–8.8 (q, 6H); 8.2–7.8 (m, H); 5.6–5.3 (m, H); 3.9–3.4 (pair of doublets, H).

EXAMPLE 2

A mixture comprising 5-methyl-2,2,4-trichloro-1,1,1-trifluorohexane (5.0 g), monoethanolamine (1.7 g) and dimethylforamide (10 ml) is heated under nitrogen in an oil bath at 105° for 2 hours. Examination of the reaction mixture by GLC shows the product to consist mainly of 2,4-dichloro-5-methyl-1,1,1-trifluorohex-2-ene.

EXAMPLE 3

A mixture comprising 5-methyl-2,2,4-trichloro-1,1,1-trifluorohexane (5.0 g), monoethanolamine (1.7 g) and dimethylacetamide (10 ml) is heated under nitrogen in an oil bath at 105° C. for 2 hours. The cooled reaction mixture is added to a large volume of water to precipitate the product. The crude product is washed with water, dried over anhydrous sodium sulphate and shown by 'Hnmr to consist almost entirely of 2,4-dichloro-5-methyl-1,1,1-trifluorohex-2-ene.

EXAMPLE 4

This is not an example of the invention but illustrates the dehydrohalogenation of the product obtained in Example 1.

2,4-Dichloro-5-methyl-1,1,1-trifluorohex-2-ene (22.1 g) in dimethylformamide (100 ml) containing lithium chloride (5.0 g) is heated under a nitrogen atmosphere in an oil bath at 160° C. for 1.5 hours. The cooled mixture is added to water (1.5 l), extracted with dichloromethane and the extracts dried over anhydrous sodium sulphate and distilled to afford 2-chloro-5-methyl-1,1,1-trifluorohexa-2,4-diene (76%). The identity of the product was proved by comparison to 'Hnmr and infra-red spectra with those of authentic material.

We claim:

1. A halogenated hydrocarbon characterised by the general formula:

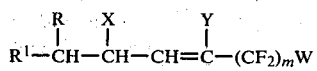

wherein

Y represents fluorine, chlorine, bromine, or —(CF$_2$)$_m$W

R represents hydrogen or lower alkyl,

R$^1$ represents lower alkyl,

X represents chlorine, bromine or iodine

W represents hydrogen, fluorine or chlorine and m is 1 or 2.

2. A halogenated hydrocarbon as claimed in claim 1 characterised in that X and Y are chlorine or bromine.

3. A halogenated hydrocarbon as claimed in claim 1 characterised in that X and Y are chlorine.

4. 2,4-Dichloro-5-methyl-1,1,1-trifluorohex-2-ene.

* * * * *